(12) United States Patent
Richart

(10) Patent No.: US 11,571,804 B2
(45) Date of Patent: Feb. 7, 2023

(54) DEVICE FOR HOLDING AND RELEASING AN OBJECT, AND RELATED METHODS

(71) Applicant: SELENIUM MEDICAL, La Rochelle (FR)

(72) Inventor: Olivier Richart, Le Bois Plage en Ré (FR)

(73) Assignee: SELENIUM MEDICAL, La Rochelle (FR)

( * ) Notice: Subject to any disclaimer, the term of this patent is extended or adjusted under 35 U.S.C. 154(b) by 191 days.

(21) Appl. No.: 16/872,668

(22) Filed: May 12, 2020

(65) Prior Publication Data
US 2020/0361076 A1 Nov. 19, 2020

Related U.S. Application Data

(60) Provisional application No. 62/847,695, filed on May 14, 2019.

(51) Int. Cl.
| | | |
|---|---|---|
| *B25J 1/00* | (2006.01) | |
| *A61B 17/68* | (2006.01) | |
| *A61B 17/17* | (2006.01) | |
| *A61B 17/00* | (2006.01) | |

(52) U.S. Cl.
CPC .............. *B25J 1/00* (2013.01); *A61B 17/1725* (2013.01); *A61B 17/686* (2013.01); *A61B 2017/00367* (2013.01)

(58) Field of Classification Search
CPC ........ B25J 1/00; B25J 1/02; B25J 1/10; A61B 17/686; A61B 2017/00367
See application file for complete search history.

(56) References Cited

U.S. PATENT DOCUMENTS

2022/0240984 A1* 8/2022 Rezach ................ A61B 17/708

FOREIGN PATENT DOCUMENTS

| EP | 2995271 A1 | 3/2016 |
| KR | 2017-0116673 A | 10/2017 |
| WO | 02/30315 A1 | 4/2002 |
| WO | 2019/030451 A2 | 2/2019 |

OTHER PUBLICATIONS

French Search Report issued in French Patent Application No. 1905009, dated Jan. 7, 2020, 2 pages.
Opinion issued in French Patent Application No. 1905009, dated May 14, 2019, 5 pages.

* cited by examiner

*Primary Examiner* — Eduardo C Robert
*Assistant Examiner* — Christina Negrellirodriguez
(74) *Attorney, Agent, or Firm* — Brown Rudmick LLP; Matthew P. York

(57) ABSTRACT

The invention relates to a device for holding and releasing an object, comprising a main body comprising a housing to at least partially accommodate said object and an opening to enable at least a portion of the object to be removed, a lid that can be moved from a closed position preventing access to said opening and an open position enabling access to said opening, and a stop mechanism designed such that it can be moved to different positions relative to the main body towards the opening of said main body, but blocked in the other direction, to enable the stop mechanism to be brought into contact with or close to the object while preventing any recoil of the stop mechanism. The invention also relates to a corresponding production method and release methods.

25 Claims, 15 Drawing Sheets

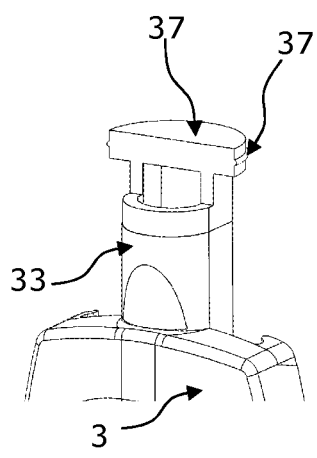 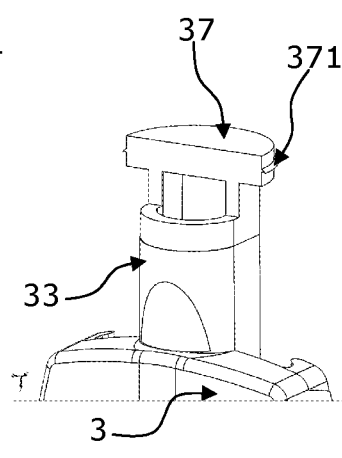 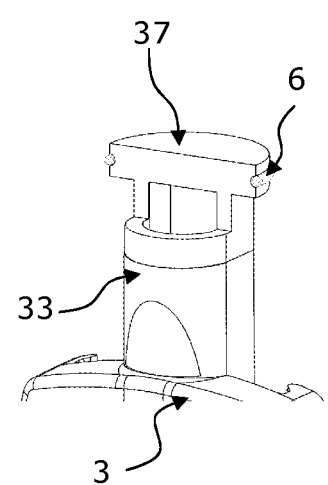
FIG.16  FIG.17  FIG.18

DEVICE FOR HOLDING AND RELEASING AN OBJECT, AND RELATED METHODS

CROSS-REFERENCE TO RELATED APPLICATIONS

This application claims priority to, and the benefit of, U.S. Provisional Application No. 62/847,695, filed May 14, 2019, and French Application No. FR 19 05009, filed May 14, 2019, the contents of each of which are incorporated by reference herein in their entireties.

FIELD OF INVENTION

The present invention relates in general to a device for holding an object such as a medical implant and for releasing said object from said device.

PRIOR ART

Devices for holding objects, which are also referred to as "grippers", are known in the prior art, in particular from international patent application WO2019030451A2 and from the French patent application filed under number FR1854199 but not yet published as of the filing date of this patent application.

The device disclosed in French patent FR1854199 enables in particular the use of a hooking assembly to hold a screw-type implant with a head that is adapted so as to abut the hooking assembly to prevent the implant from falling to the bottom of the body of the device.

However, for implants that have no head adapted so as to abut the assembly, there is a risk that the implant may slide to the bottom of the body of the device.

It is thus desirable to be able to propose another device for holding an object wherein the object can be reliably secured in a given position, while enabling it to be easily released from the device.

SUMMARY OF THE INVENTION

To this end, a device for holding and releasing an object is proposed herein, said device comprising a main body with a housing for accommodating, at least partially, said object, and an opening enabling at least a portion of said object to be extracted, characterized in that said device for holding and releasing the object also comprises:
  an attached lid that can be moved from a closed position preventing access to said opening and an open position enabling access to said opening,
  a stop mechanism designed such that it can be moved to different positions relative to the main body towards the opening of said main body, but blocked in the other direction, to enable the stop mechanism to be brought into contact with or close to the object while preventing any recoil of the stop mechanism.

The device for holding and releasing an object also provides a lower stop vis-a-vis the object, with the position of this lower stop being adjustable so as to adapt to the length of the object while preventing any recoil of said lower stop to prevent the object from falling into the main body, which would make it difficult to extract.

When assembling the device, i.e. when placing the object in the device, at least portion of the object is inserted into the body through the opening in the body which is thus used as a passage for inserting the object into the body. Another part of the object, for example a second piece that is separate from a first piece to be inserted into the body through the opening in the body, can be accommodated in part in the stop mechanism.

Access to the opening in the main body from outside the body is then blocked or prevented by moving the lid to the closed position. Moreover, prior to moving the lid to the closed position, a sealing element can be applied to the body around the opening of said body.

When the object has been inserted into the main body, the stop mechanism is then moved up towards the object to press said object up against the lid, with the stop mechanism forming a lower stop vis-a-vis the object.

The device can also include one or more of the following characteristics used in any technically permissible combination.

According to a particular characteristic, the device comprises a pinion system designed to enable said movement of the stop mechanism towards the opening of said main body and block it in the reverse direction.

According to a particular characteristic, the stop mechanism is designed such that it can be moved respective to the main body over a length enabling at least a portion of the object to be pushed out of the main body.

According to a particular characteristic, the stop mechanism comprises a housing that can accommodate a portion of the object.

This stop mechanism housing allows in particular, by enclosing said portion of the object, to maintain the axial direction of said portion of the object.

According to a particular characteristic, the housing comprises a ring through which at least a portion of the object is able to extend, said ring being made of a different material from that of the main body.

This allows the object to be in contact with a material that is compatible with its own material, for example titanium, without having to make the entire main body of the device in this material, which can be expensive.

According to a particular aspect, the ring has an inner diameter that is slightly greater than the outer diameter of the object that passes through the ring, to act as an axial guide without any jamming of the object.

Thus, it can be foreseen that when the lid is in the open position and if there is no sealing element or if the sealing element has been removed from the opening in the body, at least the portion of the object that passes through the ring can be easily extracted from the body by tipping the opening in the body downwards.

According to a particular aspect, the ring extends back from the upper end of the main body. Advantageously, said upper end of the main body delineates a passage that can be sealed.

According to a particular aspect, the object housing comprises a portion between the ring and the stop mechanism that remains open onto the inside of the main body.

According to a particular aspect, the object housing comprises a valance that extends at least underneath the ring, and the stop mechanism comprises an end portion forming a piston that can expand in an airtight manner inside the valance.

The stop mechanism thus comprises a portion forming a piston designed to be moved inside the valance, in an airtight manner respective to the valance, towards the opening in the main body, with no possible recoil.

According to a particular aspect, the valance contains a fluid, preferably a liquid, said object being housed in a chamber defined at least by said valance and said ring, said chamber being closed at its lower end by the piston of the stop mechanism and at its upper end by the sealing element.

According to a particular aspect, the opening in the main body is sealed by a removable sealing system.

According to a particular aspect, the sealing system is coupled to the lid such that moving the lid from the closed position to the open position leads to the removal of the sealing system.

According to a particular aspect, the device comprises a stabilizing system designed to stabilize the lid in the open position and in the closed position.

According to a particular aspect, the lid is designed to remain coupled to the main body in the open position, forming a stand that enables the main body to be placed on a surface and supported by this stand, with the opening of said main body being elevated relative to said surface.

According to a particular aspect, the lid comprises a guide pin that can come into contact with one end of the object when the lid is in the closed position.

According to a particular aspect, said device comprises said object, said object being a medical object.

According to a particular aspect, said object comprises two separate pieces.

According to a particular aspect, said object is a dental object, said object comprising an implant screw and a healing cap.

In particular, the implant screw has the shape of an elongated body with a hollow end, but has no head that is wider than the diameter of the screw body.

The invention also relates to a method of assembling a device for holding and releasing an object, said device being as disclosed above, with said method comprising the following steps:

when the lid is in the open position, at least a portion of the object is inserted into the main body through the opening in said main body;

the stop mechanism is moved towards the opening of said main body, to prevent or restrict the movement of the object within the main body, with any recoil of the stop mechanism being prevented.

According to a particular aspect, said at least one portion of the object inserted into the main body through the opening being a first piece, said method comprises, prior to the step of moving the stop mechanism, a step wherein a second piece is inserted into the stop mechanism, with said step of moving the stop mechanism towards the opening of said main body bringing said second piece into contact with or close to the first piece, with any recoil of the stop mechanism being prevented. The second piece can be inserted before the first piece and inversely.

According to a particular aspect, said method comprises the step wherein a chamber of the main body wherein at least a portion of said object is housed is filled with fluid or with liquid.

According to a particular aspect, said method comprises a step wherein the opening of the main body is sealed.

According to a particular aspect, said method comprises a step wherein the lid is closed before or after moving the stop mechanism.

The invention also relates to a method of releasing an object held in a device as disclosed above, with said method comprising the following steps:

moving the lid to the open position;

extracting at least a portion of the object through the opening in the main body using a tool that cooperates with said at least one portion of the object.

According to a particular aspect, said method comprises the steps of:

pressing the stop mechanism towards the opening in the main body to bring another portion of the object close to the opening in the main body; and extracting said other portion of the object through the opening in the main body using a tool that cooperates with said other portion of the object.

The invention also relates to a method of releasing an object held in a device as disclosed above, with said method comprising the following steps:

moving the lid to the open position;

pressing the stop mechanism to push a portion of the object through the opening in the main body;

extracting said portion of the object that is protruding from the opening of the main body;

extracting another portion of the object through the opening in the main body using a tool that cooperates with said other portion of the object.

BRIEF DESCRIPTION OF THE DRAWINGS

Characteristics and advantages of the invention will also be highlighted in the following description, which is purely illustrative and non-limiting and which must be read in relation to the appended drawings, of which:

FIG. 16 is a partial view of a slider according to another embodiment according to the invention, with the upper end of the slider forming a piston shown in an axial cross-cut;

FIG. 17 is a partial view of a slider according to another embodiment according to the invention, with the upper end of the slider forming a piston shown in an axial cross-cut;

FIG. 18 is a partial view of a slider according to another embodiment according to the invention, with the upper end of the slider forming a piston shown in an axial cross-cut;

DETAILED DESCRIPTION

Figure 1:
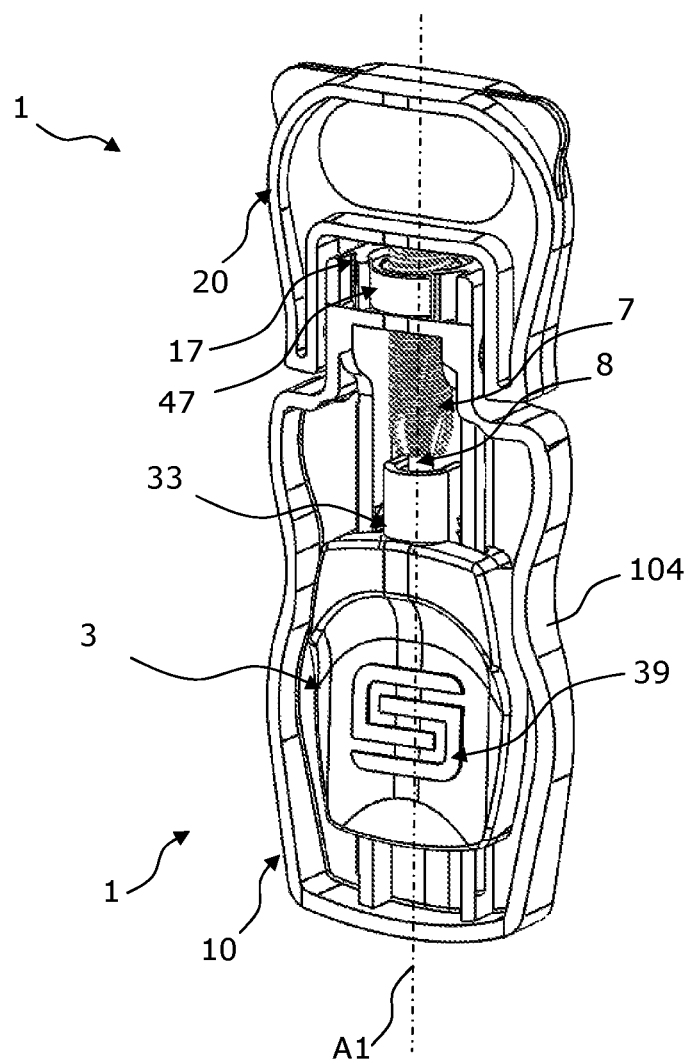
FIG. 1 is a perspective view of the front of a device according to an embodiment of the invention.

The inventive concept is described in more detail hereafter, with reference to the attached drawings, wherein embodiments of the inventive concept are shown. In the drawings, the sizes and relative sizes of the elements may be exaggerated to make them easier to see. Like numbers refer to like elements in all of the drawings. However, this inventive concept can be implemented in many different forms and should not be interpreted as being limited to the embodiments described herein. Rather, these embodiments are proposed in order to provide a complete description and convey the extent of the inventive concept to those skilled in the art. For the sake of simplification, the following embodiments are examined in relation to the terminology and structure of a device for holding and releasing an object such as a medical implant.

With reference to the illustrations, we have represented a device 1 for holding and releasing an object. In the examples shown in the illustrations, said object is a medical object, in particular a dental object, but may be another type of object.

As explained hereafter through various means of embodiment of the device, said object may comprise one or more parts, for example a medical implant and an accessory part. The device 1 can also be called a "gripper". Such a device 1 can be used by an operator to manipulate an object by means of the device in appropriate conditions of asepsis and in particular using a tool that has been adapted to extract the object.

The device 1 can be contained in a package or double packaging as described in international application WO2014188142, the content of which is incorporated as a reference into the present application, or in international application WO2018078242, the content of which is incorporated as a reference into the present application.

The device 1 comprises a main body 10 designed to enable at least a portion of said object to be accommodated, and an attached lid 20 that can be moved from a closed position wherein it prevents said object from being removed from the body to an open position wherein it enables said object to be removed or allows said object to be accessed to extract it from the body 10. According to a particular aspect, the open position also enables at least a portion of said object to be reinserted into the body 10.

The body 10 of the device 1 also comprises an opening through which the object may be removed when the lid is open.

The device 1 also comprises a stop mechanism 3 that allows the object inserted into the body of the device to be brought up against the lower stop, in particular so that it does not fall to the bottom of the body 10 of the device 1.

The device 1 is configured to enable the stop mechanism 3 to be moved towards the object (i.e. towards the opening in the body), and to prevent the stop mechanism 3 from moving away from the object (i.e. to prevent the stop mechanism 3 from recoiling from the opening in the body).

In the examples shown in the illustrations, the stop mechanism 3 is formed by a slider 3. The slider 3 can be moved along the body 10 to come into contact with the object. It can be foreseen that the slider 3 merely comes into contact with the object, but it can also be foreseen, as in the example shown in FIGS. 1 to 11, that a portion of this slider comprises a housing enabling the lower portion of the object to be accommodated. The slider 3 enables contact with the object, in particular to hold the object in place in the body and prevent it from falling to the bottom of the body. The slider 3 thus forms a lower stop that can be repositioned upwards, i.e. towards the opening of the body, to adjust to the length of the object inserted into the body of the device.

According to a particular aspect, the slider 3 can be moved over a length that enables the operator to push the object partially outside of the body 10 by moving the slider 3 towards the object when the lid 20 is in the open position. As explained hereafter, this feature is particularly useful if the object comprises two pieces of which one is supported by the slider 3. After having removed the first piece through the opening, the second piece that was previously positioned between the slider and the opening in the body may be too far from the opening in the body to be easily grasped, particularly if the grasping tool has a flange that prevents it from being inserted deeply into the body of the device or that may hinder the removal of the tool. Being able to raise the slider further and thus bring the second piece up to the opening in the body makes removal easier.

According to a particular aspect, moving the slider 3 towards the opening in the body 10 is restricted by a flange on the body 10 that is built into the upper part of said body 10.

Object Housed in the Body of the Device

As recalled above and explained hereafter through the various embodiments, said object can comprise several pieces, for example a dental implant and a healing cap.

It can be foreseen that the object comprises at least one implant screw 7 (dental implant), i.e. an elongated, threaded body, that passes through a ring 47 as explained hereafter, and optionally comprises an additional piece 8, such as a healing cap, preferably partially housed in the slider, which extends between the implant screw 7 and the slider 3. The dental implant 7 has the shape of a threaded body with the upper end positioned adjacent to the opening in the body and an inner shape adapted to cooperate with a corresponding grasping tool 9.

In the embodiments in FIGS. 1 to 11, the object thus comprises a dental implant 7 and a healing cap 8.

In the examples in FIGS. 12 to 15, only the implant 7 is shown. It can be foreseen that the implant 7 is alone or in association with a healing cap as in the embodiments shown in FIGS. 1 to 11.

Advantageously, in these embodiments in FIGS. 12 to 15, the dental implant 7 is bathed in a fluid, preferably a liquid, contained in a chamber formed by a valance 173 (for example formed by a tube) in the upper part of the body 10 of the device. The upper part of the body 10, or upper part of the slider 3, is considered to be the part of the body 10 or the part of the slider 3 that is located next to the lid 20 when the latter is in the closed position.

Before the operator opens the lid 20 or pushes the slider 3, the lower end of the valence 173 is closed by the piston 37 of the slider 3 and the upper end of the valence 173 is closed by a sealing element 273, such as a peelable strip or sheet, which can include a thermo adhesive, for example, made of a synthetic, non-woven, polyethylene fiber material, usually sold under the registered brand name TYVEK. The sealing element 273 can also be made of aluminum. Advantageously, in the initial state, i.e. when the lid 20 is in the closed position and before moving the implant 7 towards an opening, said implant 7 does not protrude from the upper end of the body 10 towards the outside of the body, but is positioned just below this level of the end of the body that is to be covered by the sealing element.

As explained hereafter, the device 1 wherein the implant screw 7, and optionally the healing cap 8, is housed, also enables the release of the implant screw 7, which can then be extracted from the device, for example using an appropriate tool 9, such as a screwdriver, comprising a tip that can fit into the head of the implant screw 7, to couple the implant screw 7 to the tool 9.

As explained hereafter, the implant screw 7 can be repositioned in its housing. In particular if the operator, such as a surgeon, needs to set the implant aside to carry out another task.

Main Body

The main body 10 comprises an opening for removal. This opening is located at one end, referred to as the upper end, of said main body 10 to allow the implant screw 7 and the healing cap 8 to be removed along an exit axis A1. As explained hereafter, this removal passage is also used to insert the implant 7 into the body of the device.

The passage by which the implant 7 is inserted into the body 10 and by which it may be removed from the body 10 can be considered as a through passage that opens into the body 10 facing the slider 3, and whose lower part can, in some embodiments, be closed by said slider 3, in particular if the passage comprises a valance 173 as in the embodiments shown in FIGS. 12 to 15 and if this valance forms a chamber with the slider 3 wherein the implant 7 bathes.

As recalled above, the other end of the chamber that holds the implant 7 is preferably closed by an element such as a sealing strip or sheet, which can be removed at the same time as or after the lid 20 is opened.

In the example shown in the illustrations, the main body 10 has an elongated shape that follows the axis A1 by which the implant 7 and the healing cap 8 are removed.

The main body 10 comprises a bottom wall 100. Advantageously, the exit axis A1 extends between the bottom wall 100 and the open front face of said body 10 which is opposite said bottom wall 100.

The bottom wall 100 comprises an inner face 101 which has ribs 13 along which the slider 3 disclosed hereafter is designed to slide towards the upper part 17 of the body 10.

Figure 3:
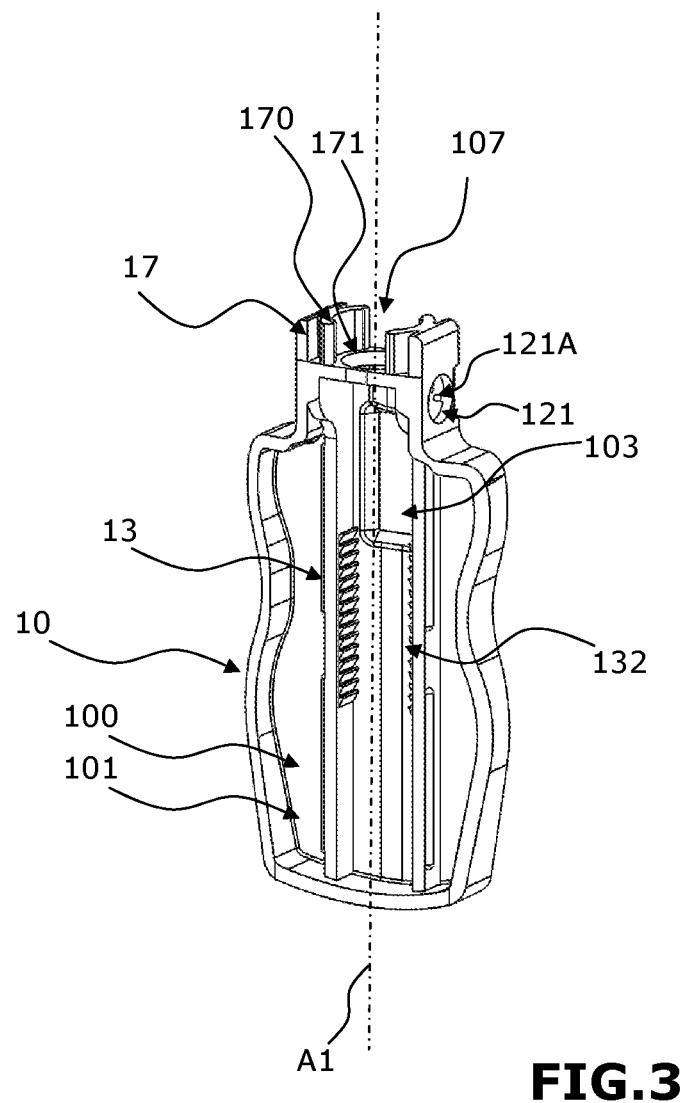
FIG. 3 is a perspective view of the body of the device shown in FIG. 1, showing the front panel of the body.
Figure 11:
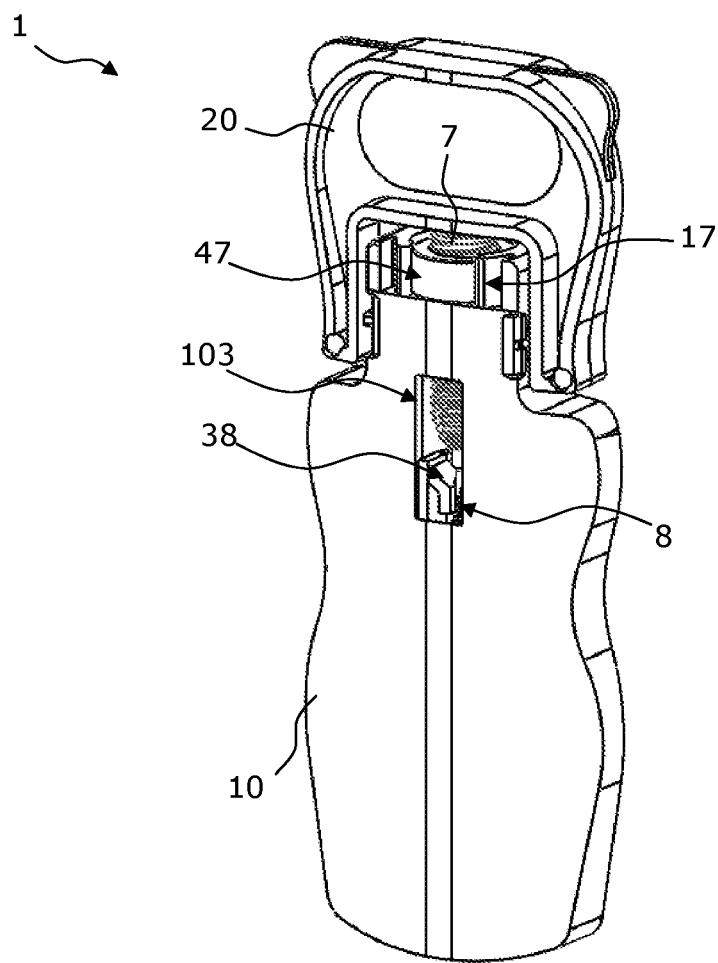
FIG. 11 is a perspective view of the back of the device according to an embodiment according to the invention, wherein a portion of the implant and of the healing cap can be seen through the window built into the back of the device.
Figure 12:
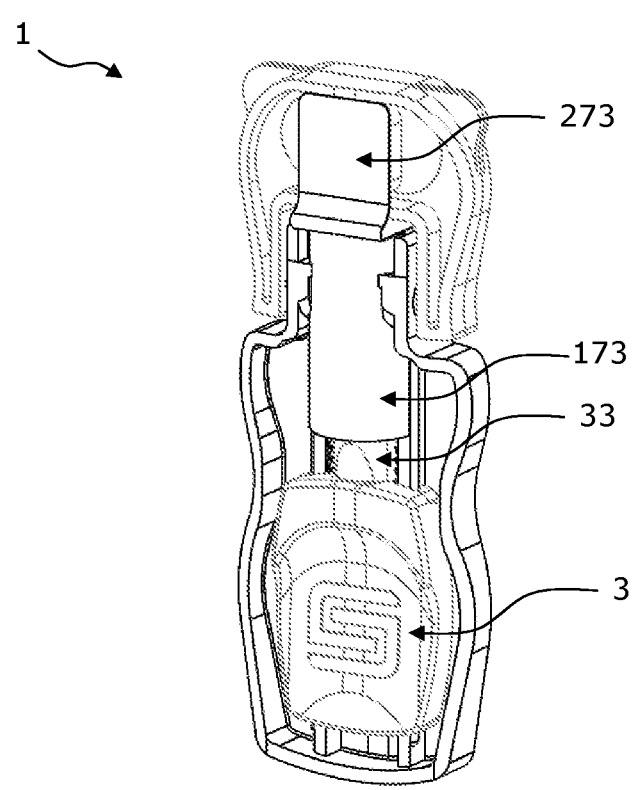
FIG. 12 is a perspective view of a device according to another embodiment.
Figure 13:
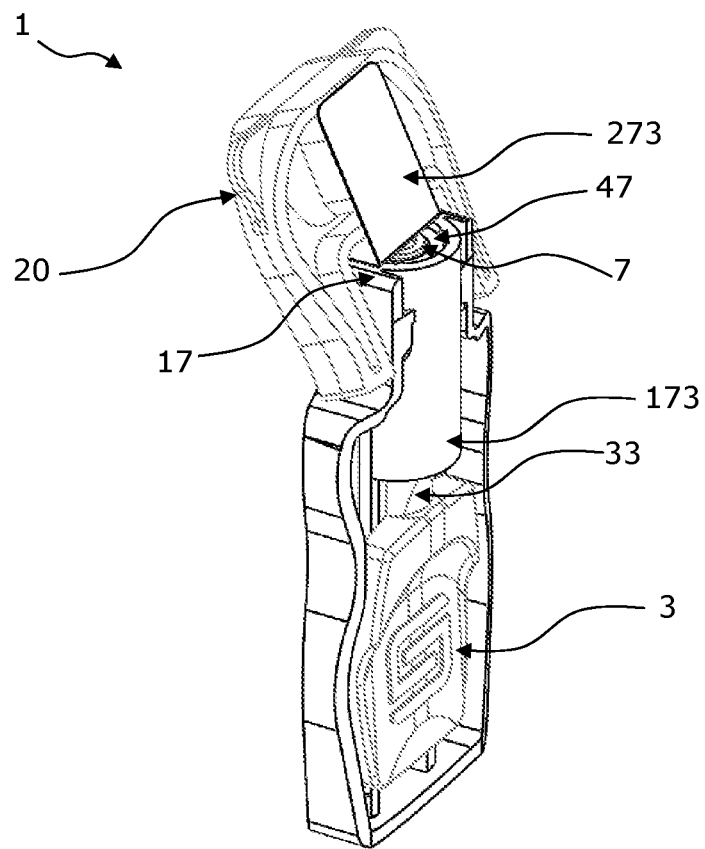
FIG. 13 is a perspective view of a device that is similar or identical to that shown in FIG. 12, with the lid in the process of being opened.
Figure 14:
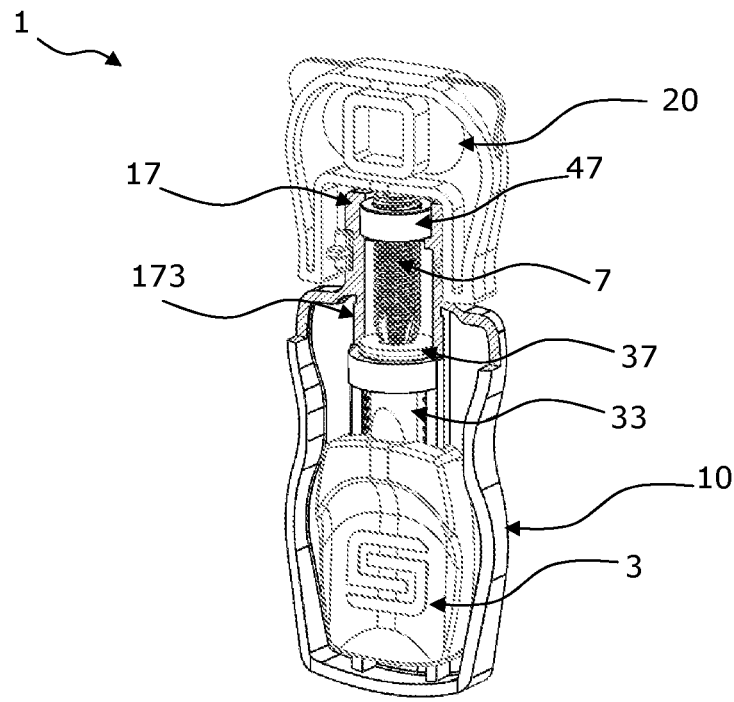
FIG. 14 is a perspective view of the device shown in FIG. 13, showing a cross-cut view of the upper part of the body of the device, with the sealing element on the opening of the body not shown, the slider shown in the lower position and equipped at its upper end with an element forming a piston that extends into the tubular housing.
Figure 15:
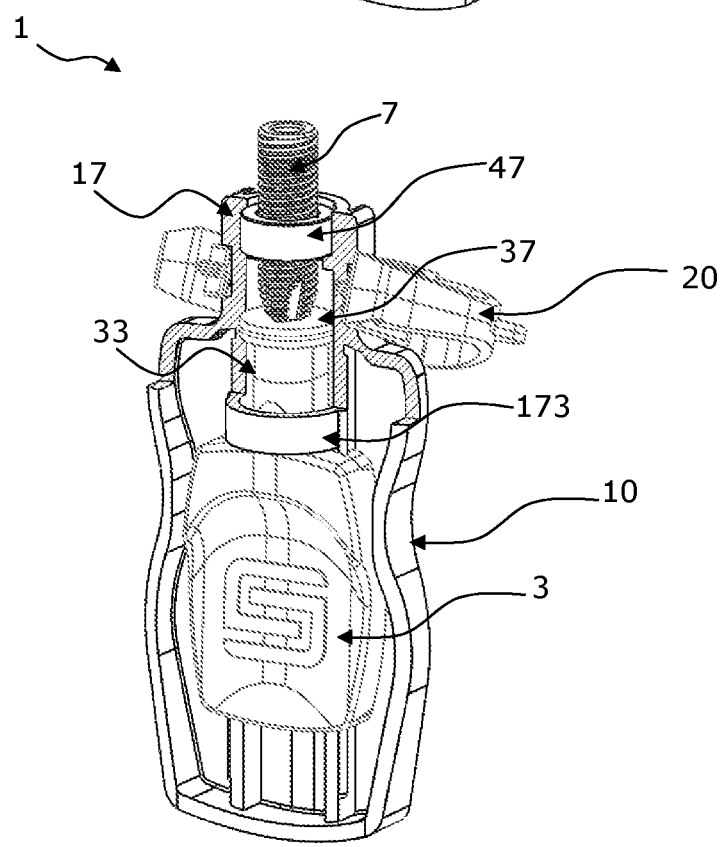
FIG. 15 is a view of the device shown in FIG. 14, with the lid open and the slider raised, such that the implant is pushed by the slider piston and protrudes from the ring in the upper part of the body.

As seen in FIG. 3 and FIG. 11, a window 103 can be built into the bottom wall 100 to make it possible to see if the object is present from the outer face 102 of said bottom wall 100. The implant 7 extends from the inner side of the bottom wall facing said window. It can be foreseen that there is no window 103.

Advantageously, the body of the device and/or the lid and/or the slider, is or are transparent or translucid.

The body 10 of the device comprises a peripheral wall 104 that extends transversally, preferably orthonagonally, to the bottom wall 101, by which the operator can grasp the body of the device. Advantageously, the opposite lateral sides of said body 10 each comprise a supplementary curved portion to make it easy for the operator to grasp said body of the device.

Slider Sliding System Respective to the Body

As indicated above, the device 1 for holding and releasing an implant comprises a sliding system for the slider 3 relative to the body 10 of the device 1.

Figure 6:
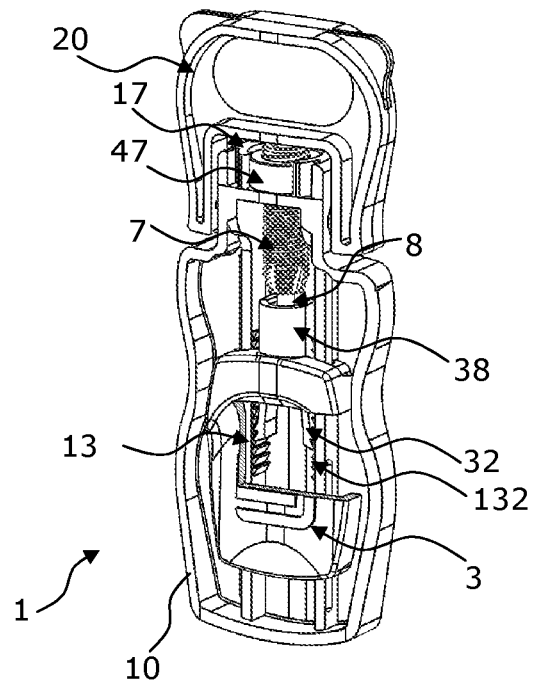
FIG. 6 is the same drawing in FIG. 1, showing a tearaway view of a portion of the slider that reveals the sliding mechanism of the slider on the body of the device.

As shown in FIGS. 3 and 6, the sliding system comprises two parallel rails 13, preferably arranged on the bottom wall 100 on the inner side of the body. To this end, the stop mechanism 3 has grooves 31 (or slots) that fit said rails. Of course, the rails 13 (ribs) can be borne by the slider 3 and the grooves or slots can be incorporated into the body 10.

In the example shown in the illustrations, the body 10 has a notching system, such as a rack and pinion system, designed to enable the movement of the slider 3 towards the upper end of the body 10 where the object is located, but preventing any recoil of the slider 3. In the example shown in the illustrations, the rack and pinion system comprises, for each rib 13, a rack 132 that fits said rib 13.

In particular, as shown in FIG. 6, a portion of the slider 3 has been indented in the middle area to show the sliding system between the slider 3 and the body 10 of the device 1.

The slider 3 comprises teeth 32 that can cooperate with the teeth in the rack and pinion system. The teeth in the rack and pinion system 132 of the body 10 and the teeth 32 of the slider 3 are angled in such a way as to allow the slider 3 to move only towards the upper end of the body of the device.

Upper Part of the Body of the Device

According to certain embodiments, the upper part 17 of the body 10 of the device 1 wherein the entrance/opening for the implant 7 is located comprises a ring 47 (also called a flange) that turns back into a corresponding housing built into the upper part 17 of the body 10 of the device 1.

Figure 4:
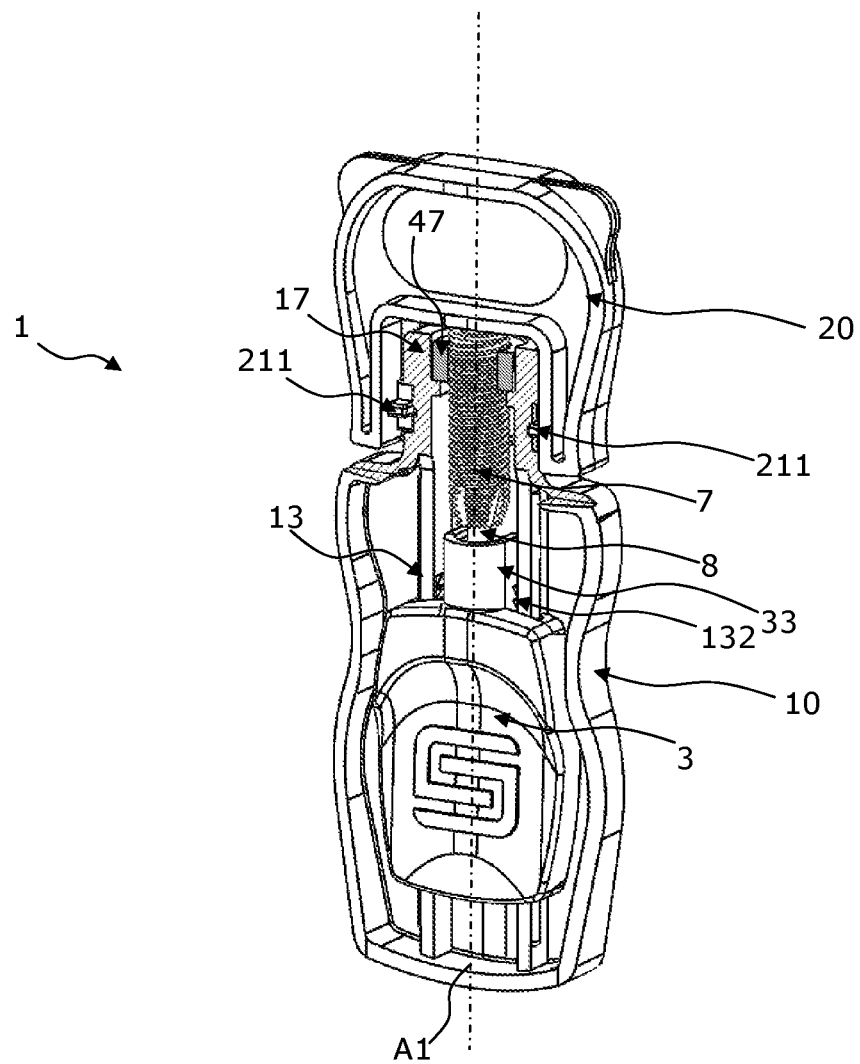
FIG. 4 is the same drawing in FIG. 1, showing an axial cross-cut view of the upper part of the body of the device.
Figure 5:
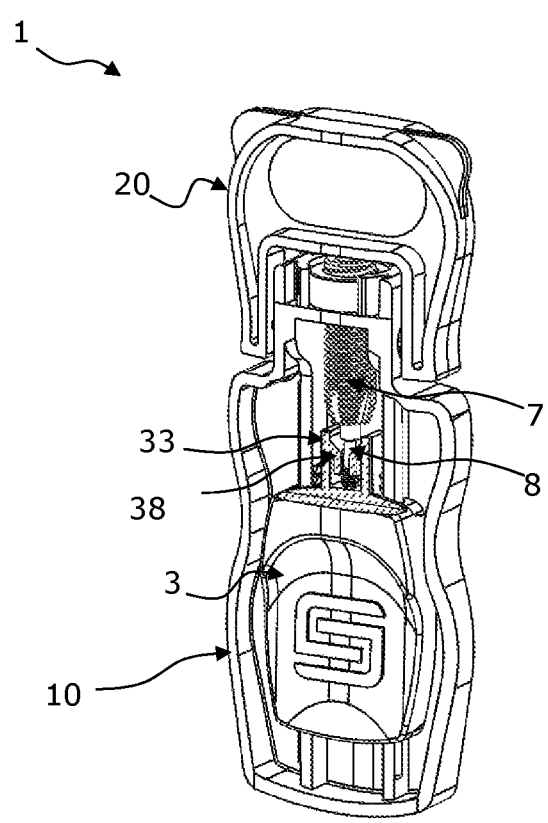
FIG. 5 is the same drawing in FIG. 1, showing an axial cross-cut view of the upper part of the slider.

FIG. 4 shows an axial cross-cut of the upper part 17 of the body of the device, which reveals the system for pivoting the lid relative to the body, as well as the ring 47.

The ring 47 is made of a different material to that of the body of the device 1. Advantageously, the ring 47 is made of a material in the same family as or that is identical to that used for the implant 7. Advantageously, the implant 7 and the piece 8 are also made of a material in the same family or an identical family. Thus it can be foreseen that the body 10 of the device is made of plastic while the ring 47 is made of titanium, since the implant 7 is made of titanium.

Such a ring enables the implant to be guided while preventing any contact between the implant and a material that would not be compatible with it.

In the examples shown in the illustrations, the upper part 17 comprises in particular a seat 171 designed to hold the ring 47. A wall 170 at least partially encloses the seat 171 to delineate the receiving seat of the ring 47. The ring 47 is preferably pressed into its corresponding receiving housing on the body 10.

The seat 171 comprises a through passage aligned with the through passage of the ring 47. The implant 7 can pass through the ring 47 and through the through passage of the seat 171.

In other words, the body 10 also comprises a housing that can hold at least a portion of the implant 7. The through passages of the ring 47 and the seat 171 form a portion of this housing through which the implant 7 can be inserted into and removed from the body 10.

Preferentially, the inner diameter of the ring 47, which is slightly greater than the outer diameter of the implant, is slightly smaller than that of the seat 171 (and of the valance 173 when it is present as explained hereafter) to prevent any risk of contact between the implant 7 and the material in the body of the device.

In the embodiments shown in FIGS. 1 to 11, and when the lid 20 is in the closed position, a portion of the implant 7 extends below the receiving seat 171 of the ring 47 and can be seen by an operator looking at the front of the body, in particular if the front face of the body (opposite the bottom wall) is open. The implant 7 is in contact with the piece 8 that is partially held in the upper part of the slider 3.

In the embodiments shown in FIGS. 12 to 15, and when the lid 20 is in the closed position, the portion of the implant 7 extending below the receiving seat of the ring 47 is enclosed by the valance 173 inside which the upper end of the slider 3 is engaged, forming a piston.

The upper part 17 of the body 10 thus comprises, by means of the ring 47 and the through passage of the seat 171, an opening, referred to as the insertion/release opening of the implant 7 (whose upper portion can be sealed pending the opening of the lid). As recalled above, this opening also allows the screw 8 to be removed and the slider 3 can be moved, if necessary, to bring the screw 8 closer to the exit opening.

The insertion/release axis or the exit axis A1 of the implant 7 corresponds, in the example shown in the illustrations, to the longitudinal axis of the body 10 of the device.

In other words, when the operator is holding the device facing him, i.e. with the lid 20 pivoted towards him, the insertion/release opening of the body of the device is located substantially on the side of the operator.

Having one end of the object extending inside the body and the other end covered by the lid when said lid is in the closed position enables the object to be properly held and protected.

Lid

In the examples shown in the illustrations, the lid 20 is in the general shape of an upside-down "U".

The lid 20 thus comprises two arms 21 connected by a connecting part 22 that can be grasped by the operator. The lid 20 is coupled to the body 10 by its arms 21.

Figure 8:
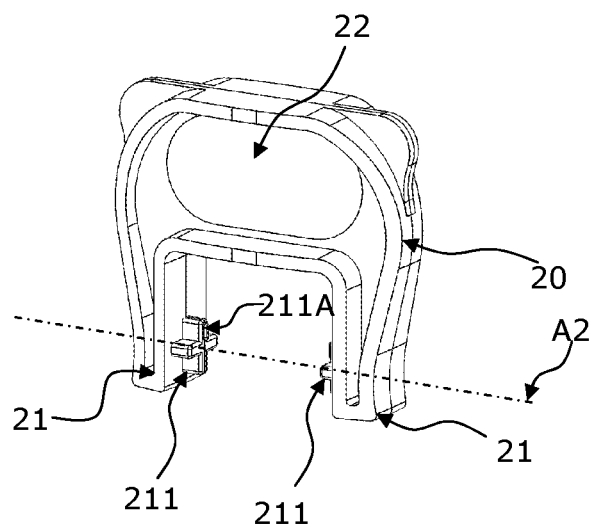
FIG. 8 is a view of the lid of a device according to an embodiment of the invention.

As shown more particularly in FIGS. 8 and 3, each arm 21 comprises an element 211, for example a male and female element in the form of crosspieces, that can cooperate with a corresponding female element 121 on the body 10 to enable the lid 20 to be pivoted relative to the body 10.

The lid 20 is pivoted around an axis A2 that is orthogonal to the axis A1 along which the object is removed from the body 10. In particular in the example shown in the illustrations, the pivot axis A2 is parallel to the median plane of the body (or to the median sliding plane of the slider 3).

The pivoting elements 211, 121 built into the lid 20 and the body 10 allow the lid 20 to be pivoted respective to the body 10, to either side of the exit axis A1. In other words, the lid 20 can be pivoted to either side of the median plane of the body 10 that passes through this exit axis A1.

Figure 20:
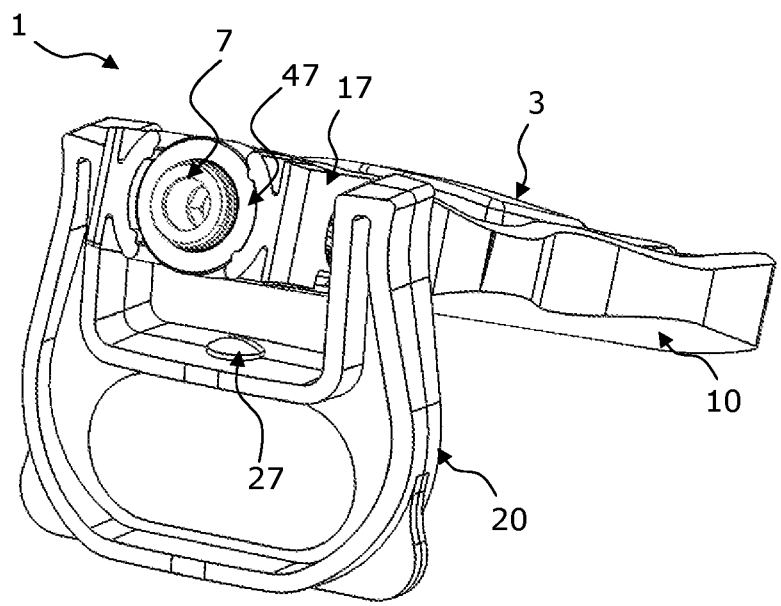
FIG. 20 is a side view of a device according to an embodiment of the invention showing the lid in the open position with the implant housed in the body of the device with one end protruding slightly through the ring.
Figure 21:
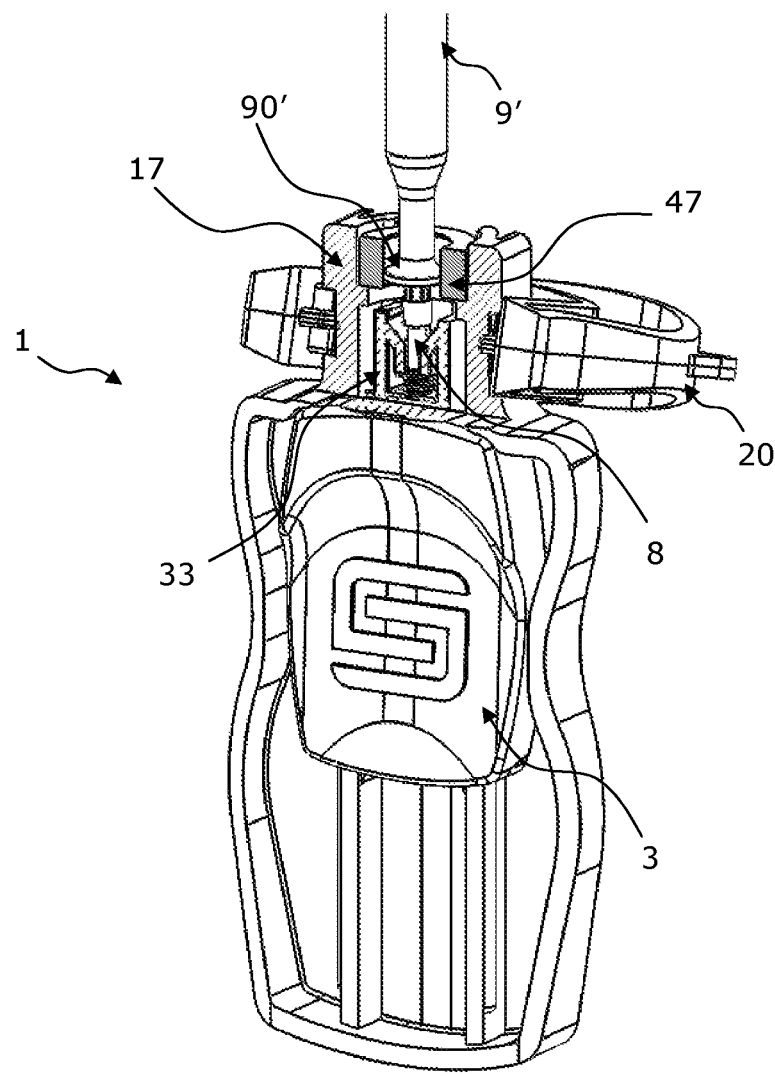
FIG. 21 is a perspective view of a device according to an embodiment of the invention, with the lid in the open position and the slider pushed to the upper position to bring the healing cap up near the opening of the body, with a tool being inserted through the ring to grasp the healing cap and extract it from the body of the device.

The connecting part 22 of the lid 20 comprises an inner edge which, when the lid 20 is in the closed position, is positioned facing the exit opening 107 of the body 10. As shown more particularly in FIG. 10 and FIG. 20, said inner edge of the lid 20 has a surface 27 that extends towards said opening, preferably with a convex curve, for example in the shape of a half-sphere, in order to fit into the hollow end of the implant 7 and thus ensure that the implant is axially centered in the opening.

System for Setting the Lid Positions

The open and closed positions of the lid 20 are preset stable positions (discretes). In other words, the operator must apply a force beyond a threshold value in order to cause the lid 20 to pivot from one position to another.

When in the closed position, the lid 20 prevents or hinders any access to the object by the operator in order to prevent any unintentional removal or deterioration of the object.

A portion of the mechanism enabling pivoting between the lid 20 and the body 10 is built into the upper part 17 of the body 10 of the device. In particular, in the example shown in the illustrations, said pivoting mechanism is located near the receiving seat 171 and comprises two elements 112 placed on either side of said seat 171 on the upper lateral edges of said body 10.

In the example shown in the illustrations, the pivoting mechanism comprises a position setting system allowing the lid 20 to be pivoted into positions wherein it is secured (kept stable), preferably also when the lid 20 is pivoted to either side.

The lid 20 position setting system also offers a setting system corresponding to the closed position of the lid 20, which enables the lid 20 to be kept in this closed position, as long as the operator does not force the lid 20 into another set position corresponding to an open position of the lid, in either direction.

These stabilized positions are obtained in the examples shown in the illustrations by at least one of the arms of the crosspieces which comprises a tooth 211A (seen in FIG. 8) that can fit into the grooves 121A of an element 121 built into the body 10 (see FIG. 3), in function of the angular position of the lid 20 respective to the body 10. To this end, the element 121 comprises three recesses that are angularly spaced respective to each other according to the desired stable positions of closure, opening to one side and opening to the other side.

Thus, by turning the lid 20 relative to the body 10, the lid 20 is moved to a new stable position by fitting the tooth 121A on each crosspiece 121 into one of the recesses 122A of the corresponding element 121 on the body 10.

The pivoting and setting elements 211, 121 can be positioned indiscriminately on the lid 20 and the body 10. Thus, in the examples in the illustrations, the crosspieces are moved by the arms 21 of the lid 20 while the corresponding housings of these crosspieces are built into the body 10. But positioning the crosspieces on the body and the corresponding housings on the arms of the lid can also be foreseen.

The connecting part 22 of the lid 20 comprises a flat portion that can bear an inscription such as a logo, allowing the lid to be customized.

Figure 19:
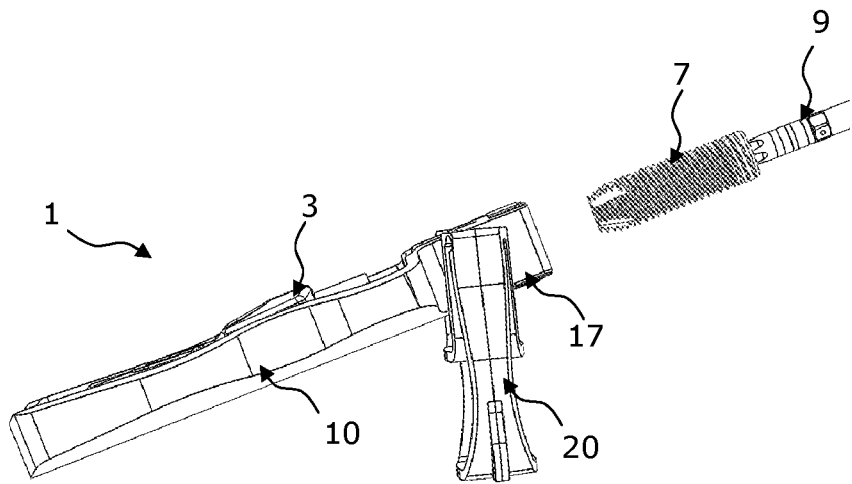
FIG. 19 is a side view of a device according to an embodiment of the invention showing the lid in the open position with the implant being removed from the body of the device using an appropriate grasping tool.

The operator can thus pivot the lid 20 into a preset, stable, open position, preferably either to one or the other side of the device. The lid 20 thus pivoted forms a base that can be used to set the device on a surface, such as a table, so that the body of the device is tilted respective to the surface on which it is set, as shown in FIG. 19. Advantageously, the body of the device is tilted respective to the surface on which it is set, at an angle of about 30°. It should be understood that this angle depends on the length of the body and the preset stable positions into which the lid 20 can be pivoted respective to the body 10 of the device. Preferentially, when in the open position, the lid forms an angle of 90° relative to the body 10.

The upper part 17 of the body 10 through which the implant 7 is to be removed is thus elevated away from the surface on which the device is set.

Slider

As recalled above, the slider's mobility enables the slider's position to be adjusted to the position and length of the object formed by the set of pieces 7, 8 such that the pieces 7 and 8 can be brought into contact with each other by raising the slider until the upper piece 7 comes into contact with the lid 20 (if there is no sealing element between the lid and the opening in the body).

The setting that prevents the slider from recoiling makes it possible to ensure that object 7, 8 is secured between the slider 3 and the lid 20 as long as the latter has not been moved to an open position, which prevents any or all of the object from falling into the bottom of the body 10 or into an area of the body 10 that is not intended to accommodate the object.

When raised up against the pieces 7, 8, the slider 3 forms a lower stop while the lid (or an intermediate sealing element as described hereafter) forms an upper stop.

When the lid is in the open position, the slider 3 also allows the object formed by the set of pieces 7, 8 to be pushed along the axis A1 in such a way as to bring the end of the piece 8, which is in contact with the slider 3, up to the upper part 17 of the body, so that the implant screw 7 and the healing cap 8 can be removed from the body 10.

In this exit position of the slider 3 and when the piece 7 has been removed, the piece 8 of the object is close to and facing the through passage of the ring 47, which enables the operator to grasp the piece 8 using a tool 9' by inserting said tool through 47.

According to some embodiments, the lid 20, the body 10 and the slider 3 are designed such that the length of the implant, i.e. at least its ends, can be seen. The length of the implant can thus be seen by the operator that looks at the front of the device, i.e., on the slider side, in the normal grasping position of the device.

The slider comprises a zone 39 for placing a finger, also referred to as a fingerhold, for example with surface areas that are recessed or raised, such as ribs or ridges, which makes it easier for the operator to slide the slider 3.

Upper Portion of the Slider

The slider 3 comprises an upper portion 33 that corresponds to the end portion of the slider 3 that is facing the opening 107 of the body 10.

Figure 2:
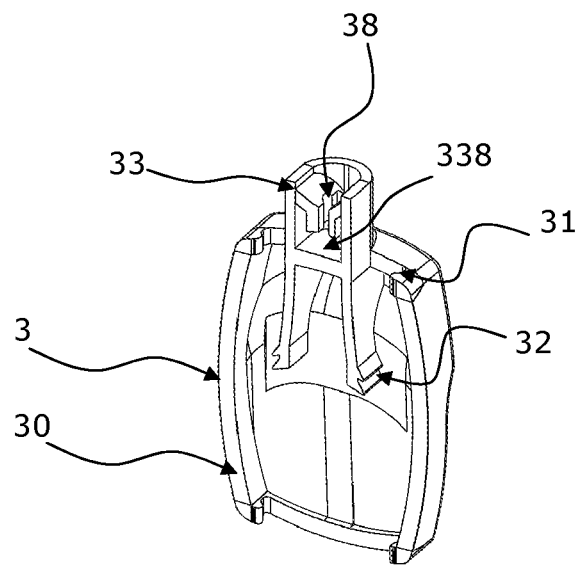
FIG. 2 is a perspective view of the inner side of the slider of the device shown in FIG. 1.
Figure 9:
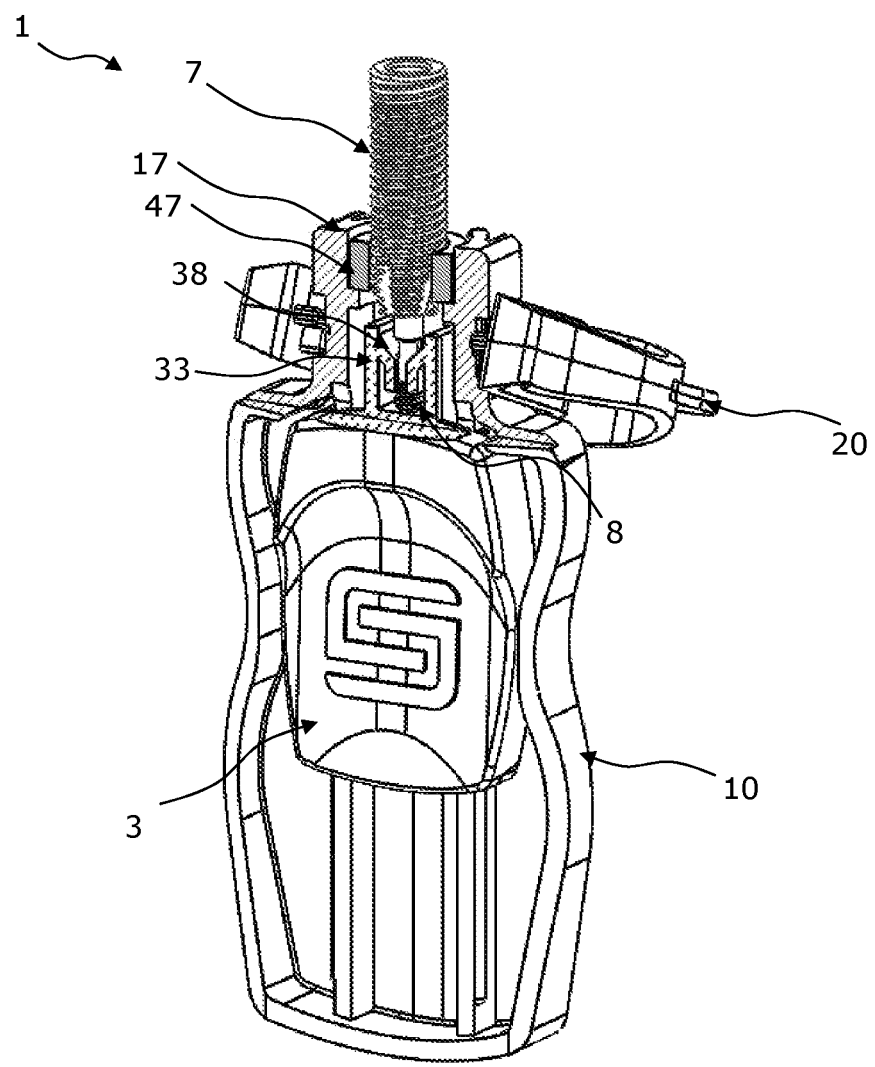
FIG. 9 is the same drawing in FIG. 8, showing a cross-cut view of the upper part of the body of the device and of the upper part of the slider.

As can be seen more particularly in FIG. 2 and FIG. 9, the upper portion 33 comprises a receiving portion 38 enabling a portion of the piece 8 to be accommodated.

In the example shown in FIGS. 1 to 11, the receiving portion 38 is in the shape of a funnel and the end of this piece 8 opposite the implant is positioned facing and/or in contact with a portion 338 of the slider which forms the lower stop for the piece 8. The portion 338 thus enables the piece 8 to be stopped so as to restrict or control its insertion into the slider 3 to keep a portion of the piece 8 extended outside the slider, in particular outside of the funnel 38 so that it comes into contact with the piece 7.

Examples of Use of the Embodiments in FIGS. 1 to 11

In the example shown in FIGS. 1 to 11, during the assembly of the device with the insertion of the implant screw 7 and the healing cap 8 into the body of the device, the healing screw 8 can be inserted into the corresponding housing 38 of the slider 3, without having to pass it through the ring 47, for example by inserting it from the open side of the body of the device in the upper end of the slider 3, which is then in the lower position, i.e. near the lower part of the body 10.

Then the implant screw 7 can be inserted into the upper part of the body 10 through the corresponding exit opening 107 (see FIG. 3), in a position such that upper end of the screw is positioned near the upper end of the body, and wherein the ring 47 encloses said implant screw (i.e., the implant screw does not fully extend below the ring).

The lid 20 can be closed to form an upper stop for the implant screw 7. The implant screw 7 and the healing cap 8 are then placed in contact with each other by raising the slider 3 towards the implant screw 7, which also blocks the implant screw 7 against the lid 20.

Figure 10:
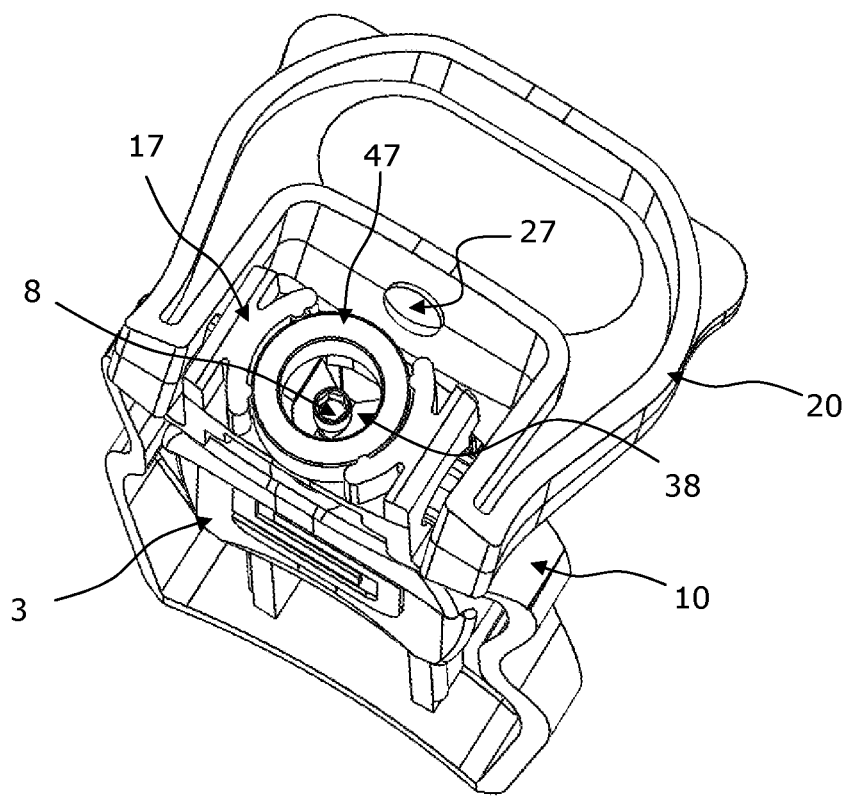
FIG. 10 is a perspective view of the top of the device shown in FIG. 9, with the implant removed and the healing cap still inside the upper part of the slider.

When removing the implant 7, the implant 7 is extracted without removing the healing cap 8. As shown in FIG. 10, the healing cap 8 remains supported by the portion of the end 33 of the slider 3, and can be extracted from the body when the implant screw 7 has been removed. In other words, in the examples shown in the illustrations, there is no particular mechanical coupling between the implant screw 7 and the healing cap 8.

Thus, a device corresponding to that shown for example in FIG. 1 is obtained.

When the operator wishes to remove the pieces 7, 8 from the device 1, he can then open the lid 20 to access the implant 7 through the opening in the body 10, removing the implant 7 for example using the tool 9 that is adapted to couple with the implant, for example by coupling a male end of the tool to a hollow end of the implant 7.

Figure 7:
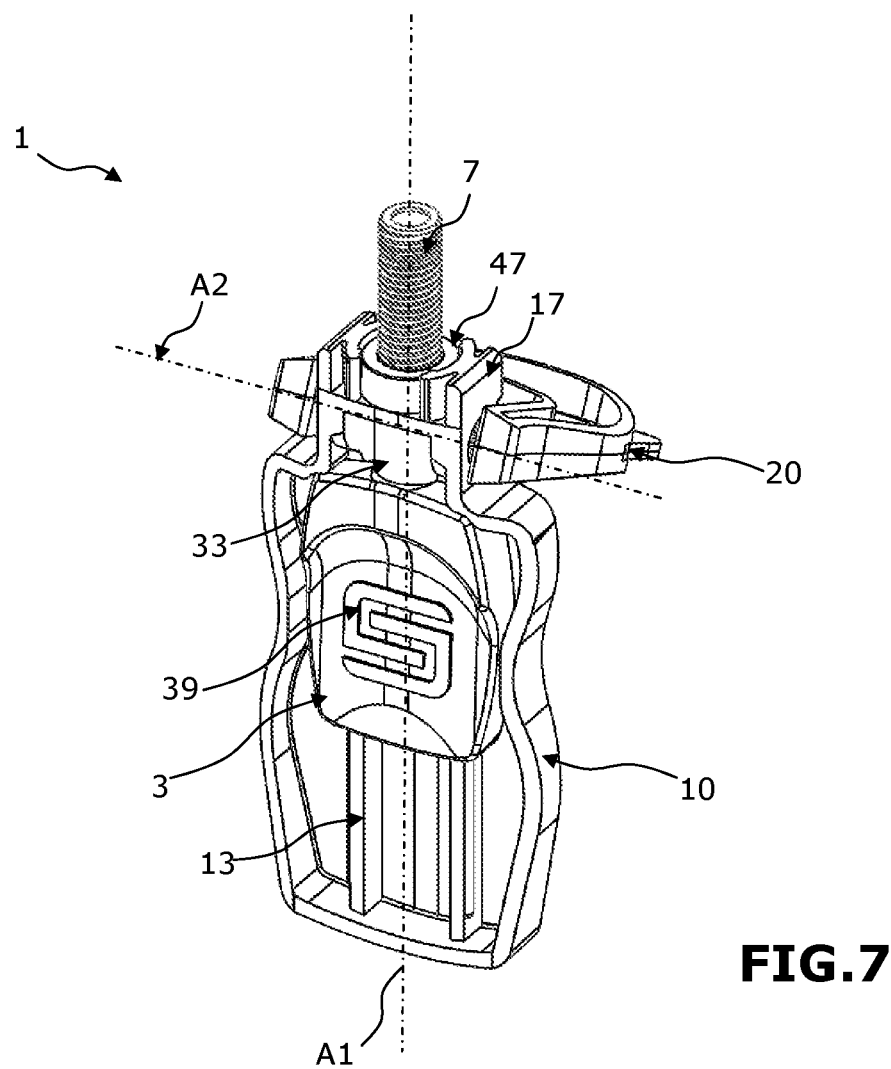
FIG. 7 is a perspective view of the device shown in FIG. 1, with the lid open and with the slider in the upper position such that the implant screw is partially protruding from the opening in the device.

As shown in FIGS. 7, 9, the operator can also push the slider 3 to push the implant 7 out and grasp it. It should be noted that removing the implant 7 by pushing the slider 3 enables the implant to be grasped, either manually or with an appropriate tool, by its outer edge.

As shown in FIG. 10, pushing the slider 3 enables the piece 8 to be brought up to the opening of the body 10. In particular, the operator can then pass an appropriate tool 9' through the ring 47 to retrieve the piece 8 and remove it from the slider and the body.

It should be noted that pushing the slider 3 to the upper position makes it easy to extract the healing cap because otherwise the 90° flange of the tool 9' could catch against the ring 47 or the seat 171 of the ring when attempting to bring the tool 9' back out if it is inserted too deeply into the body 10 of the device 1.

Examples of Use of the Embodiments in FIGS. 12 to 15

In the examples in FIGS. 12 to 15, the piston 37 of the slider 3 is inserted into the lower part of the valance 173. It can be foreseen that the piston also has an appropriate shape, such as the shape of the upper part 33 with the funnel 38 and the lower stop mechanism 338 in the embodiment shown in FIG. 2, so as to accommodate a piece such as the piece 8 shown in the embodiments in FIGS. 1 to 11, while retaining its function as a piston, i.e., with an outer edge adapted to sliding tightly into the valance 173.

In particular, it can be foreseen as shown in FIGS. 16 to 18, that the tightness is ensured by an outer element formed by a peripheral section of the edge of the piston head with semi-circular cross-section 371 (FIG. 16), a quarter-round section 371' (with a curve turned to the upper inside) (FIG. 17) or formed by a seal 6 (FIG. 18), preferably with a circular cross-section, set into the peripheral slot built into the edge of the piston head.

An axial groove or slot can be built into the ring to make it easy to remove the air when pushing the piston 37 into the valance 173.

The implant 7 is inserted into the valance 173 via the opening in the body 10 through the ring 47. Advantageously, a portion of the implant remains enclosed by the ring 47.

According to a particular aspect, the chamber delineated at least by the valence 173 and the piston 37 is filled with liquid, for example a sodium chloride solution allowing a highly hydrophilic condition to be preserved over the entire implant surface, or a surfactant enabling an active surface state to be maintained and not changed in contact with air, or a bone growth boosting agent, such as a BMP (Bone Morphogenetic Protein), or a disinfecting agent/preventive bactericide (silver ion solution or other), wherein the implant 7 bathes. The opening in the body 10 is in this case sealed to retain the liquid and the lid can be turned to the closed position facing the opening.

The operator that wishes to remove the implant 7 and the piece 8 when present, can then open the lid and, preferably simultaneously, remove the sealing element 273, to access the screw. The implant 7 (and the piece 8 if present) can then be removed as previously explained using an appropriate tool 9, with or without pushing on the slider 3.

Pushing on the slider 3 also pushes out the liquid wherein the implant is bathed, like a syringe wherein the plunger would be the piston 37.

Preferentially, the sealing element 273 used is attached to the lid 20, so that when the lid 20 is opened the sealing element 273 is removed from the opening in the body of the device. Thus the illustration of the lid being opened in FIG. 12 reveals the upper end of the implant 7 which is enclosed in the ring 47 and the valance 173, with the sealing element 273 having been broken or removed from the upper end of the implant housing relative to the body 10, when the lid 20 was being opened.

As an alternative, it can be foreseen that the sealing element is not connected to the lid and is to be pulled off manually to free the opening 10 and thus open the chamber containing the implant 7.

Throughout the specification, reference to "an embodiment" means that any particular function, structure, or characteristic described in relation to an embodiment is included in at least one embodiment of the present invention. Thus, the appearance of the expression "in an embodiment" in various places throughout the specification does not necessarily refer to the same embodiment. Moreover, the particular functions, structures or characteristics can be combined in any appropriate way in one or more embodiments.

The invention is not limited to the embodiments shown in the drawings.

In addition, the term "comprising" does not exclude other elements or steps. Moreover, the characteristics or steps that have been described with reference to one of the embodiments described above can also be used in combination with other characteristics or steps in other embodiments described above.

The invention claimed is:

1. A device for holding and releasing an object, said device comprising:
   a main body with a housing for at least partially accommodating the object;
   an opening that allows at least a portion of said object to be extracted from the main body;
   a lid attached to the main body that can be moved from a closed position preventing access to said opening and an open position providing access to said opening; and
   a stop mechanism designed such that the stop mechanism can be moved to different positions relative to the main body towards the opening of said main body, but blocked in the other direction, to enable the stop mechanism to be brought into contact with or close to the object while preventing any recoil of the stop mechanism.

2. The device according to claim 1, further comprising a pinion system configured to enable said movement of the stop mechanism towards the opening of said main body and block it in the reverse direction.

3. The device according to claim 1, wherein the stop mechanism is configured such that it can be moved respective to the main body over a length enabling at least a portion of the object to be pushed out of the main body.

4. The device according to claim 1, wherein the stop mechanism comprises a housing that can accommodate a portion of the object.

5. The device according to claim 1, wherein the housing of the main body comprises a ring through which at least a portion of the object is able to extend, said ring being made of a different material from that of the main body.

6. The device according to claim 5, wherein the housing of the main body comprises a portion between the ring and the stop mechanism that remains open into the interior of the main body.

7. The device according to claim 5, wherein the housing of the object comprises a valance that extends at least underneath the ring, and the stop mechanism comprises an end portion forming a piston that can expand in an airtight manner inside the valance.

8. The device according to claim 7, wherein the valence contains a fluid, preferably a liquid, said object being housed in a chamber defined at least by said valence and said ring, said chamber being closed at its lower end by the piston of the stop mechanism and at its upper end by the sealing element.

9. The device according to claim 1, wherein the opening of the main body is sealed by a peelable sealing system.

10. The device according to claim 9, wherein the sealing system is coupled to the lid such that moving the lid from the closed position to the open position leads to the removal of the sealing system.

11. The device according to claim 1, further comprising a stabilizing system is configured to stabilize the lid in an open position and in a closed position.

12. The device according to claim 1, wherein the lid is designed to remain coupled to the main body, in the open position, forming a stand that enables the main body to be placed on a surface and supported by this stand, with the opening of said main body being elevated relative to said surface.

13. The device according to claim 1, wherein the lid comprises a guide pin that can come into contact with one end of the object when the lid is in the closed position.

14. The device according to claim 1, wherein said device comprises said object, said object being a medical object.

15. The device according to claim 14, wherein said object comprises two separate pieces.

16. The device according to claim 15, wherein said object is a dental object, said object comprising an implant screw and a healing cap.

17. A method for assembling a device for holding and releasing an object according to claim 1, said method comprising the following steps:

inserting at least a portion of a medical object into the main body through the opening in said main body when the lid is in the open position; and moving the stop mechanism towards the opening of said main body to prevent or restrict the movement of the object within the main body, with any recoil of the stop mechanism being prevented.

18. The method according to claim 17, wherein said at least one portion of the object inserted into the main body through the opening is a first piece.

19. The method according to claim 18, further comprising, prior to the step of moving the stop mechanism, inserting a second piece of the object into the stop mechanism, wherein said step of moving the stop mechanism towards the opening of said main body brings said second piece of the object into contact with or close to the first piece of the object, with any recoil of the stop mechanism being prevented.

20. The method according to claim 17, further comprising filling a chamber of the main body in which at least a portion of said object is housed with fluid or liquid.

21. The method according to claim 17, further comprising sealing the opening of the main body.

22. The method according to claim 17, further comprising closing the lid before or after moving the stop mechanism.

23. A method for releasing an object held in a device according to claim 1, said method comprising the following steps:

moving the lid to the open position; and extracting at least a first portion of an object through the opening in the main body using a tool that cooperates with said at least first portion of the object.

24. A method according to claim 23, further comprising the following steps:

pressing the stop mechanism towards the opening in the main body to bring another portion of the object close to the opening in the main body; and extracting at least a second portion of the object through the opening in the main body using a tool that cooperates with said second portion of the object.

25. A method for releasing an object held in a device according to claim 1, said method comprising the following steps:

moving the lid to the open position;

pressing the stop mechanism to push a portion of the object through the opening in the main body;

extracting said portion of the object that is protruding from the opening of the main body; and extracting another portion of the object through the opening in the main body using a tool that cooperates with said other portion of the object.

\* \* \* \* \*